United States Patent [19]

Seymour

[11] Patent Number: 5,225,401
[45] Date of Patent: Jul. 6, 1993

[54] TREATMENT OF CONGESTIVE HEART FAILURE

[75] Inventor: Andrea A. Seymour, Pennington, N.J.

[73] Assignee: E. R. Squibb & Sons, Inc., Princeton, N.J.

[21] Appl. No.: 744,208

[22] Filed: Aug. 12, 1991

[51] Int. Cl.$^5$ .................... A61K 37/02; C07K 5/06
[52] U.S. Cl. .................... 514/19; 514/18; 514/114; 514/412; 514/423
[58] Field of Search .................... 514/19, 18, 114, 412, 514/423

[56] References Cited

U.S. PATENT DOCUMENTS

| | | | |
|---|---|---|---|
| 4,722,810 | 2/1988 | Delaney et al. | 260/402.5 |
| 4,749,688 | 6/1988 | Haslanger et al. | 514/19 |
| 4,801,609 | 1/1989 | Haslanger et al. | 514/506 |
| 4,818,749 | 4/1989 | Gold et al. | 514/19 |
| 4,826,816 | 5/1989 | Andrews et al. | 514/19 |
| 4,906,615 | 3/1990 | Berger | 514/19 |

FOREIGN PATENT DOCUMENTS 361365 4/1990 European Pat. Off. .
2207351 2/1989 United Kingdom .

OTHER PUBLICATIONS

Physicians' Desk Reference, 45 Edition, 1991, pp. 1513-1516 and 2141-2143.
Jour. Am. Soc. of Nephrology, 23rd Annual Meeting, Dec., 1990, Abstract 44P.
Margulies et al., "Neutral Endopeptidase...", Kidney International, vol. 38 (1990), pp. 67-72.
Federation of American Societies for Experimental Biology, Apr. 1991, Abstract 3775.
Seymour et al., "Effects of Renal Perfusion Pressure...", Amer. Physiological Society, 1987, F234-F238.
Deedwania, "Angiotension-Converting Enzyme...", Arch. Intern. Med., vol. 150, 1990, 1798-1805.
Cavero et al., "Cardiorenal Actions Of Neural...", Circulation, vol. 82, No. 1, Jul. 1990, pp. 196-201.
Cody, "Pharmacology of Angiotensin-Converting Enzyme...", Amer. Jour. of Cardio., vol. 66, 7D-13D, Oct. 1990.
Cohn, "Mechanism In Heart Failure...", Amer. Jour. of Cardiology, vol. 66, 2D-6D, Oct. 1990.
Gottlieb et al., "Renal Effects of Angiotensin...", Amer. Jour. of Cardiology, vol. 66, 14D-21D, Oct. 1990.
Seymour et al., "Potentiation of Renal Effects...", Hypertension, vol. 14, No. 1, pp. 87-97, 1989.

*Primary Examiner*—Lester L. Lee
*Attorney, Agent, or Firm*—Stephen B. Davis

[57] ABSTRACT

Congestive heart failure is treated by administration of a selective inhibitor of neutral endopeptidase and an angiotensin converting enzyme inhibitor. Captopril, fosinopril sodium, enalapril maleate and lisinopril are the preferred angiotensin converting enzyme inhibitors and the mercapto compounds of the formula

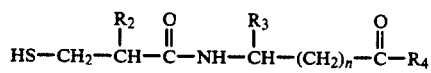

$$HS-CH_2-CH-C-NH-CH-(CH_2)_n-C-R_4$$

with $R_2$, $R_3$ substituents and carbonyl groups as shown are the preferred selective inhibitors of neutral endopeptidase.

7 Claims, No Drawings

TREATMENT OF CONGESTIVE HEART FAILURE

BACKGROUND OF THE INVENTION

Congestive heart failure occurs as a result of impaired pumping capability of the heart and is associated with abnormal retention of water and sodium. It results in an inadequate supply of blood and oxygen to the body's cells. The decreased cardiac output causes an increase in the blood volume within the vascular system. Congestion within the blood vessels interferes with the movement of body fluids in and out of various fluid compartments, and they accumulate in the tissue spaces, causing edema.

The angiotensin converting enzyme inhibitor captopril has been approved by the United States Food and Drug Administration for the treatment of congestive heart failure. In many cases it is utilized in patients receiving digitalis, as well as diuretic treatment. The angiotensin converting enzyme inhibitor enalapril maleate has been approved by the United States Food and Drug Administration as adjunctive therapy in the management of heart failure for use along with diuretics and digitalis.

Delaney et al. in U.S. Pat. No. 4,722,810 disclose enkephalinase inhibiting compounds of the formula

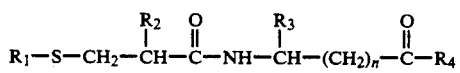

wherein $R_1$ is hydrogen or acyl; $R_2$ is lower alkyl, aryl, aralkyl, heterocycloalkyl, or cycloalkylalkyl; $R_3$ is hydrogen, lower alkyl, aryl, aralkyl, heterocycloalkyl, or cycloalkylalkyl; n is an integer from 1 to 15, and $R_4$ is hydroxy, lower alkoxy, aralkoxy, etc. Delaney et al. in U.K. Patent Application 2,207,351A disclose that such compounds possess neutral endopeptidase inhibitor activity and produce diuresis, natriuresis, and lower blood pressure. Delaney et al. in U.K. 2,207,351A also disclose that the neutral endopeptidase inhibitors can be administered in combination with other blood pressure lowering agents, for example, an angiotensin converting enzyme inhibitor such as captopril, zofenopril, fosinopril, enalopril, lisinopril, etc.

Cavero et al., "Cardiorenal Actions of Neutral Endopeptidase Inhibition in Experimental Congestive Heart Failure", Circulation, Vol. 82, p. 196-201 (1990) reported that the administration of the neutral endopeptidase inhibitor SQ28,603, i.e. (N-[2-(mercaptomethyl)-1-oxo-3-phenylpropyl-β-alanine), in anesthetized dogs with congestive heart failure induced by rapid right ventricular pacing resulted in diuresis and natriuresis. The authors conclude that these studies support an important therapeutic role for neutral endopeptidase inhibitors in congestive heart failure.

Haslanger et al. in U.S. Pat. No. 4,749,688 disclose the method of treating hypertention with neutral metalloendopeptidase inhibitors alone or in combination with atrial peptides or angiotensin converting enzyme inhibitors. Haslanger et al. in U.S. Pat. No. 4,801,609 disclose mercaptoacylamino acids useful in the treatment of hypertension and congestive heart failure.

Delaney et al. in European Patent Application 361,365 Al disclose that neutral endopeptidase inhibiting aminobenzoic acid compounds produce diuresis, natriuresis, and lower blood pressure and are additionally useful in the treatment of congestive heart failure.

Delaney et al. further disclose that these neutral endopeptidase inhibitors can be administered in combination with other blood pressure lowering agents such as angiotensin converting enzyme inhibitors, i.e., captopril, zofenopril, fosinopril, enalapril, lisinopril, etc.

SUMMARY OF THE INVENTION

This invention is directed to the method of treatment of congestive heart failure with the combination of a selective inhibitor of neutral endopeptidase and an angiotensin converting enzyme inhibitor. These agents may be administered in a single dose or administered separately within a short period of time of each other.

DETAILED DESCRIPTION OF THE INVENTION

This invention is directed to the treatment of congestive heart failure with a selective inhibitor of neutral endopeptidase and an angiotensin converting enzyme inhibitor.

The term "selective inhibitor of neutral endopeptidase" refers to compounds whose activity as an inhibitor of neutral endopeptidase is at least 100 fold greater than the activity of the same compounds as an inhibitor of the angiotensin converting enzyme. Neutral endopeptidase inhibitor activity can be determined, for example, according to the procedure developed by Dr. M. Asaad (unpublished) in which the inhibition of the cleavage of the Dansyl-Gly-Phe-Arg substrate by neutral endopeptidase isolated from rat kidney is assessed using a fluorometric assay. Angiotensin converting enzyme inhibitor activity can be determined, for example, according to the procedure described by Cushman et al. in Biochem. Pharmacol., Vol. 20, p. 1637-1648 (1971).

Suitable selective neutral endopeptidase inhibitors for use in practicing the method of treatment of this invention are those of the formula

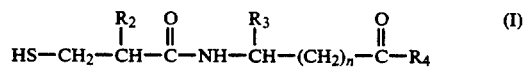

and pharmaceutically acceptable salts thereof wherein $R_2$ is lower alkyl of 1 to 7 carbons,

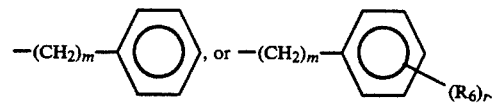

$R_3$ is hydrogen, lower alkyl of 1 to 7 carbons,

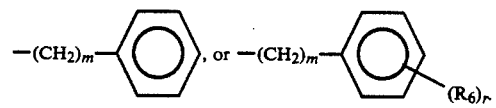

$R_4$ is hydroxy, lower alkoxy of 1 to 7 carbons, or $NH_2$.

n is an integer from 1 to 15.

m is zero or an integer from 1 to 4.

$R_6$ is lower alkyl of 1 to 4 carbons, lower alkoxy of 1 to 4 carbons, lower alkylthio of 1 to 4 carbons, hydroxy, Cl, Br, F, or $CF_3$.

r is an integer from 1 to 3 provided that r is more than one only if $R_6$ is hydroxy, methyl, methoxy, Cl or F.

Preferred are the selective neutral endopeptidase inhibitors of formula I wherein
$R_2$ is benzyl,
$R_3$ is hydrogen,
n is an integer from 1 to 9, and
$R_4$ is hydroxy.

The compound reported in the literature as SQ28,603, which is the compound of formula I wherein
$R_2$ is benzyl,
$R_3$ is hydrogen,
n is one, and
$R_4$ is hydroxy is the most preferred for use in the method of treatment of this invention.

The preparation of the compounds of formula I is taught by Delaney et al. in U.S. Pat. No. 4,722,810.

Suitable angiotensin converting enzyme inhibitors for use in the method of treatment of this invention include the mercaptoalkanoyl prolines described by Ondetti et al. in U.S. Pat. Nos. 4,046,889 and 4,105,776 such as captopril, 1-[(2S)-3-mercapto-2-methylpropionyl]-L-proline. Also suitable are the acylthioalkanoyl and mercaptoalkanoyl ether and thioether substituted prolines described by Ondetti et al. in U.S. Pat. No. 4,316,906 such as zofenopril calcium, [1(R*),2α, 4α]-1-[3-(benzoylthio)-2-methyl-1-oxopropyl]-4-(phenylthio)-L-proline, calcium salt; mercaptoalkanoyl thiazolidinecarboxylic acid such as rentiapril, (2R,4R)-2-(o-hydroxypheny)-3-(3-mercaptopropionyl)-4-thiazolidinecarboxylic acid; and acylthio compounds such as pivopril, (S)-(−)-N-cyclopentyl-N-[3-[(2,2-dimethyl-1-oxopropyl)thio]-2-methyl-1-oxopropyl]glycine; and alacepril, N-[1-[(S)-3-mercapto-2-methylpropionyl]-L-prolyl]-3-phenyl-L-alanine, acetate ester.

Other suitable angiotensin converting enzyme inhibitors are phosphinylalkanoyl substituted prolines described by Petrillo in U.S. Pat. No. 4,337,201 such as fosinopril sodium, (4S)-4-cyclohexyl-1-[[(R)-[(S)-1-hydroxy-2-methylpropoxy](4-phenylbutyl) phospinyl]-acetyl]-L-proline, propionate ester, sodium salt; and phosphinate substituted prolines described by Karanewsky et al. in U.S. Pat. Nos. 4,452,790 and 4,745,196 such as ceronapril, (S)-1-[6-amino-2-[[hydroxy(4-phenylbutyl) phosphinyl]oxy]-1-oxohexyl]-L-proline.

Other suitable angiotensin converting enzyme inhibitors are carboxyalkyl derivatives as described by Harris et al. in U.S. Pat. No. 4,374,829 such as enalapril maleate, 1-[N-[(S)-1-carboxy-3-phenylpropyl]-L-alanyl]-L-proline, 1′-ethyl ester, maleate (1:1); and lisinopril, 1-[N²-[(S)-1-carboxy-3-phenylpropyl]-L-lysyl]-L-proline dihydrate; as described by Attwood et al. in U.S. Pat. No. 4,512,924 such as cilazapril, (1S,9S)-9-[[(S)-1-carboxy-3-phenylpropyl]-amino]octahydro -10-oxo-6H-pyridazino1,2a][1,2]diazepine-1-carboxylic acid, 9-ethyl ester, monohydrate; as described by Gold et al. in U.S. Pat. No. 4,587,256 such as ramipril, (2S,3aS,6aS)-1-[(S)-N-[(S)-1-carboxy-3-phenylpropyl]alanyl]octahydrocyclopenta[b]pyrrole-2-carboxylic acid, 1-ethyl ester; as described by Oka et al. in U.S. Pat. No. 4,385,051 such as delapril hydrochloride, ethyl (S)-2-[[(S)-1-[(carboxymethyl)-2-indanylcarbamoyl]ethyl]amino]-4-phenylbutrate, monohydrochloride; as described by Hoefle et al. in U.S. Pat. No. 4,344,949 such as quinapril hydrochloride, (S)-2-[(S)-N-[(S)-1-carboxy-3-phenylpropyl]alanyl]1,2,3,4-tetrahydro-3-isoquinolinecarboxylic acid, 1-ethyl ester, monohydrochloride, monohydrate; and as described by Vincent et al. in U.S. Pat. No. 4,508,729 such as perindopril, (2S,3aS,7aS)-1-[(S)-N-[(S)-1-carboxybutyl]alanyl]hexahydro-2-indolinecarboxylic acid. Other suitable angiotensin converting enzyme inhibitors include spirapril hydrochloride, (8S)-7[[(S)-1-[(S)-1-carboxy-3-phenylpropyl]alanyl]1,4-dithia-7-azaspiro [4.4]nonane-8-carboxylic acid, 1-ethyl ester, monohydrochloride; indolapril hydrochloride, (2S,3aS,7aS)-1-[(S)-N-[(S)-1-carboxy3-phenylpropyl]alanyl]hexahydro -2-indolinecarboxylic acid, 1-ethyl ester, monohydrochloride; benazepril hydrochloride, (3S)-3-[[(1S)-1-carboxy-3-phenylpropyl ]amino]-2,2,4,5-tetrahydro-2-oxo-1H-1-benzazepine-1-acetic acid, 3-ethyl ester, monohydrochloride; and libenzapril, N-[(3S)-1(carboxymethyl)-2,3,4,5-tetrahydro-2-oxo-1H-1-benzazepin-3-yl]-L-lysine.

Preferred angiotensin converting enzyme inhibitors for use in the method of treatment of this invention are captopril, fosinopril sodium, enalapril maleate, or lisinopril. Captopril is the most preferred angiotensin converting enzyme inhibitor for use in the method of treatment of this invention.

According to this invention, the selective neutral endopeptidase inhibitor and the angiotensin converting enzyme inhibitor may be administered from a single dosage form containing both types of compounds, may be administered in separate dosage forms taken at the same time, or may be administered separately on a carefully coordinated schedule. If administered separately, the two inhibitors can be administered from within several minutes of each other up to about 4 hours apart.

The selective neutral endopeptidase inhibitor can be administered at a dosage range of from about 0.03 to about 1000 mg. per kg. of body weight per day with a dosage range of from about 0.3 to about 300 mg. per kg. of body weight per day being preferred. The angiotensin converting enzyme inhibitor can be administered at a dosage range of from about 0.001 to about 50 mg. per kg. of body weight with a dosage range of from about 0.1 to about 10 mg. per kg. of body weight being preferred.

Both inhibitors can be administered orally, parenterally, or one orally and the other parenterally. Each inhibitor may be administered from one to about four times per day depending upon the duration of activity of the inhibitor and the severity of the congestive heart failure.

The inhibitors can be formulated, in the amounts described above, according to accepted pharmaceutical practice with a physiologically acceptable vehicle, carrier, excipient, binder, preservative, stabilizer, flavor, etc., in the particular type of unit dosage form.

Illustrative of the adjuvents which may be incorporated in tablets are the following: a binder such as gum tragacanth, acacia, corn starch or gelatin; an excipient such as dicalcium phosphate or cellulose; a disintegrating agent such as corn starch, potato starch, alginic acid of the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as stabilizer, sucrose as sweetening agent, methyl and propyl parabens as preservatives, a dye and a flavoring such as cherry or orange.

The following demonstrate the effectiveness of a preferred embodiment of the invention.

Experimental

A series of studies were conducted in dogs which were paced for 7 to 14 days and a second series of studies were performed approximately 3 weeks after pacing was begun.

1. Surgical Procedures

The dogs used in the studies were chronically instrumented for hemodynamic measurements before and during rapid ventricular pacing. Three to four weeks before a study, dogs were subjected to surgical procedures for implantation of a ventricular lead and pacemaker generator, vascular catheter for the measurement of blood pressure, and ultrasonic flow probes for determination of blood flow rates. During the first surgery, a catheter was implanted into one femoral artery for measurement of mean arterial pressure (MAP). The free end of the catheter was attached to the reservoir of a vascular access port positioned subcutaneously on the dog's hip. In the second procedure, performed one to two weeks later, a sutureless pacing lead was implanted into the apex of the heart. The lead was connected to a programmable pacing generator. On the same day, a flow probe was positioned around the ascending aorta for measurement of aortic flow, an estimate of cardiac output (CO). Silastic catheters were inserted directly into the right and left atrial appendages and connected to vascular access ports. These catheters allowed measurement of right atrial pressure (RAP) and left atrial pressure (LAP). During a third surgical procedure, the left renal artery was isolated and a flow probe was applied to provide means for direct and continuous measurement of renal blood flow (RBF).

2. Data Collection

On the morning of a experiment, a Foley catheter was inserted into the dog's urinary bladder. During the course of each study, urine was collected at timed intervals for determination of urine volume (UV) and for measurement of sodium concentration by ion-selective electrodes. Excretion rates of this electrolyte was calculated and expressed as $\mu$Eq/min.

The reservoirs of the three vascular access ports were punctured using Huber needles which were connected via tubing to transducers for measurement of MAP, LAP and RAP. The flow probes on the ascending aorta and on the renal artery were connected to a dual-channel flow meter for determination of the blood flow through these vessels. Data from the pressure transducers and flow meter were acquired every 5 seconds and were used to calculate stroke volume (aortic flow/heart rate), systemic vascular resistance (SVR=[MAP-RAP]/aortic flow) and renal vascular resistance (RVR=[MAP-RAP]RBF). The hemodynamic data for each 30 minute period were averaged and presented as a single value for that time.

A venous catheter was placed percutaneously for administration of creatinine (50 mg/kg+1 mg/kg/min, iv). Approximately 45-60 minutes after starting the creatinine infusion, the urinary bladder was flushed with 20 ml. of sterile distilled water and the first urine collection was begun. Urine was collected and the bladder was flushed at 30 minute intervals throughout the remainder of the experiment. Blood samples were collected in heparin at the midpoint of each 30 minute period and the hematocrit was measured. The concentrations of creatinine were determined in each of these urine and plasma samples by spectrophotometric assay and the renal clearance of creatinine was calculated as an estimate of the glomerular filtration rate (GFR) for each 30 minute period.

3. Studies

Studies were conducted in 10 dogs 7 to 14 days after beginning pacing of the left ventricle at a rate of 260 beats/min. Dogs were used in more than one study after an appropriate time interval. The treatments tested were (n represents the number of dogs in each study):

a) 1 ml/kg of the 0.84% sodium bicarbonate vehicle (n=6);
b) 10 $\mu$mol/kg, iv (28.5 mg/kg) of SQ28,603 (n=8);
c) 100 $\mu$mol/kg of captopril (n=4); and
d) 100 $\mu$mol/kg of captopril then 10 $\mu$mol/kg of SQ28,603 administered 30 minutes later (n=5).

The data collected in the 7 to 14 day study appears in Table 1.

Additional studies were conducted in 10 dogs paced at 260 to 220 beats/min for 21 to 24 days. Again, dogs were used in more than one study following an appropriate time interval. The treatments tested were (n represents the number of dogs in each study):

a) 1 ml/kg of the 0.84% sodium bicarbonate vehicle (n=5);
b) 10 $\mu$mol/kg, iv (28.5 mg/kg) of SQ28,603 (n=5);
c) 10 $\mu$mol/kg of captopril (n=4); and
d) 10 $\mu$mol/kg of captopril and 10 $\mu$mol/kg of SQ28,603 administered 30 minutes apart (n=8).

The data collected in the 21 to 24 day study appears in Table 2.

For each study, two 30-minute control periods were observed, a blood sample was obtained for hormonal measurements and the dog was treated intravenously with 1 ml/kg of vehicle (0.84% NaHCO$_3$), 10 $\mu$mol/kg of SQ28,603, captopril (doses given below) or the combination of captopril and 10 $\mu$mol/kg SQ28,603. Thereafter, urine collections and midpoint blood samples were obtained at 30 minute intervals while blood for hormonal assays were drawn two and four hours after administration of the NEP inhibitor. A portion of each urine sample was also reserved for measurement of cyclic GMP concentration so that urinary excretion of cyclic GMP was calculated for each 30 minute period. Urinary and plasma concentrations of ANP and cyclic GMP and plasma renin activity were determined by radioimmunoassays.

Significant differences between the effects of vehicle and SQ28,603 were determined by analysis of variance or analysis of covariance for each time point. All data are given as the mean± standard error of the mean.

TABLE 1

Hemodynamic, renal and hormonal responses to SQ28,603 in dogs treated with captopril during thre first week of rapid ventricular pacing

| Time (min) | Right Atrial Pressure (mm Hg) | | | |
| --- | --- | --- | --- | --- |
| | Vehicle | SQ 28,603 | Captopril | Captopril + SQ 28,603 |
| | (n = 6) | (n = 8) | (n = 5) | (n = 4) |

TABLE 1-continued

Hemodynamic, renal and hormonal responses to SQ28,603
in dogs treated with captopril during thre first week
of rapid ventricular pacing

| | | | | |
|---|---|---|---|---|
| Baseline | 12.2 ± 1.4 | 13.0 ± 1.7 | 12.8 ± 1.0 | 11.8 ± 0.9 |
| Captopril | 12.0 ± 1.4 | | 12.1 ± 1.6 | 12.0 ± 0.8 |
| SQ 28,603 | | | | |
| 30' | 12.4 ± 1.1 | 12.9 ± 1.6 | 11.2 ± 1.6 | 12.1 ± 1.1 |
| 60' | 12.6 ± 1.2 | 12.6 ± 1.7 | 11.5 ± 1.6 | 10.8 ± 1.1 |
| 90' | 12.6 ± 1.1 | 11.4 ± 1.6 | 12.1 ± 1.4* | 9.6 ± 1.4* |
| 120' | 12.5 ± 1.4 | 12.2 ± 2.1 | 11.8 ± 1.5 | 8.8 ± 1.5 |
| 150' | 13.2 ± 1.4 | 13.0 ± 2.9 | 12.6 ± 1.5 | 9.2 ± 1.6 |
| 180' | 12.9 ± 1.5 | 12.2 ± 2.4 | 11.9 ± 1.4 | 9.6 ± 1.9 |
| 210' | 12.7 ± 1.7 | 11.2 ± 1.3 | 11.8 ± 1.2 | 11.0 ± 2.0 |

Change from Baseline (mm Hg)

| Vehicle | SQ 28,603 | Captopril | Captopril + SQ 28,603 |
|---|---|---|---|
| 0.2 ± 1.3 | −0.1 ± 0.3 | −1.6 ± 0.8 | 0.3 ± 1.0 |
| 0.4 ± 0.7 | −0.4 ± 0.3 | −1.4 ± 0.8 | −1.0 ± 1.0 |
| 0.3 ± 1.6 | −1.6 ± 0.7 | −0.8 ± 0.5 | −2.2 ± 1.4 |
| 0.2 ± 0.7 | −0.8 ± 0.9 | −1.0 ± 0.7 | −3.0 ± 1.1 |
| 0.9 ± 0.8 | 0.0 ± 1.6 | −0.2 ± 0.6 | −2.6 ± 1.4 |
| 0.6 ± 0.6 | −0.8 ± 1.4 | −0.9 ± 0.7 | −2.2 ± 1.9 |
| 0.5 ± 0.6 | −1.8 ± 1.3 | −1.0 ± 0.4 | −0.8 ± 2.1 |

Mean Arterial Pressure (mm Hg)

| Time (min) | Vehicle | SQ 28,603 | Captopril | Captopril + SQ 28,603 |
|---|---|---|---|---|
| | (n = 6) | (n = 8) | (n = 5) | (n = 4) |
| Baseline | 96 ± 3 | 98 ± 4 | 94 ± 2 | 96 ± 6 |
| Captopril | 100 ± 3 | | 85 ± 2 | 88 ± 6 |
| SQ 28,603 | | | | |
| 30' | 99 ± 4 | 101 ± 4* | 88 ± 3* | 83 ± 7 |
| 60' | 95 ± 4 | 103 ± 4* | 87 ± 3 | 79 ± 7 |
| 90' | 94 ± 3 | 101 ± 5* | 90 ± 3* | 81 ± 4 |
| 120' | 94 ± 3 | 104 ± 4* | 92 ± 4* | 85 ± 3 |
| 150' | 96 ± 4 | 104 ± 4* | 92 ± 4* | 88 ± 3 |
| 180' | 96 ± 3 | 103 ± 4* | 92 ± 3* | 89 ± 3 |
| 210' | 96 ± 4 | 102 ± 4* | 93 ± 4* | 88 ± 5 |

Change from Baseline (mm Hg)

| Vehicle | SQ 28,603 | Captopril | Captopril + SQ 28,603 |
|---|---|---|---|
| 2 ± 3 | 3 ± 1 | −6 ± 2* | −14 ± 3* |
| −1 ± 2 | 4 ± 2* | −8 ± 2* | −17 ± 2* |
| −2 ± 2 | 3 ± 2* | −4 ± 1 | −15 ± 2* |
| −2 ± 3 | 5 ± 1* | −2 ± 2 | −11 ± 3* |
| −1 ± 4 | 6 ± 1 | −2 ± 3 | −8 ± 4 |
| 0 ± 3 | 5 ± 1 | −2 ± 2 | −7 ± 3 |
| 0 ± 4 | 4 ± 2 | −1 ± 3 | −8 ± 2 |

Cardiac Output (l/min)

| Time (min) | Vehicle | SQ 28,603 | Captopril | Captopril + SQ 28,603 |
|---|---|---|---|---|
| | (n = 6) | (n = 8) | (n = 5) | (n = 4) |
| Baseline | 1.32 ± 0.09 | 0.94 ± 0.06 | 1.15 ± 0.18 | 0.94 ± 0.15 |
| Captopril | 1.28 ± 0.09 | | 1.14 ± 0.21 | 1.02 ± 14* |
| SQ 28,603 | | | | |
| 30' | 1.31 ± 0.09 | 0.87 ± 0.07 | 1.16 ± 0.18 | 1.37 ± 0.16 |
| 60' | 1.44 ± 0.15 | 0.91 ± 0.09 | 1.06 ± 0.16 | 1.42 ± 0.18 |
| 90' | 1.35 ± 0.12 | 0.93 ± 0.09 | 1.05 ± 0.16 | 1.13 ± 0.10 |
| 120' | 1.39 ± 0.12 | 0.94 ± 0.09 | 1.11 ± 0.17 | 1.07 ± 0.12 |
| 150' | 1.37 ± 0.11 | 0.92 ± 0.08 | 1.11 ± 0.17 | 0.94 ± 0.10 |
| 180' | 1.38 ± 0.12 | 0.96 ± 0.08 | 1.06 ± 0.17 | 0.93 ± 0.08 |
| 210' | 1.50 ± 0.12 | 1.03 ± 0.11 | 1.08 ± 0.17 | 0.97 ± 0.13 |

Change from Baseline (l/min)

| Vehicle | SQ 28,603 | Captopril | Captopril + SQ 28,603 |
|---|---|---|---|
| −0.01 ± 0.02 | −0.06 ± 0.03 | 0.00 ± 0.04 | 0.43 ± .05* |
| 0.12 ± 0.12 | −0.03 ± 0.04 | −0.09 ± 0.08 | 0.48 ± .11* |
| 0.03 ± 0.08 | −0.01 ± 0.05 | −0.10 ± 0.07 | 0.19 ± .10 |
| 0.07 ± 0.08 | −0.00 ± 0.04 | −0.05 ± 0.07 | 0.13 ± 0.11 |
| 0.05 ± 0.08 | −0.02 ± 0.04 | −0.04 ± 0.09 | 0.00 ± 0.08 |
| 0.06 ± 0.08 | 0.02 ± 0.05 | −0.10 ± 0.08 | −0.01 ± 0.06 |
| 0.18 ± 0.13 | 0.09 ± 0.09 | −0.07 ± 0.08 | 0.03 ± 0.07 |

Stroke Volume (ml/beat)

| Time (min) | Vehicle | SQ 28,603 | Captopril | Captopril + SQ 28,603 |
|---|---|---|---|---|

TABLE 1-continued

Hemodynamic, renal and hormonal responses to SQ28,603
in dogs treated with captopril during thre first week
of rapid ventricular pacing

|  | (n = 6) | (n = 8) | (n = 5) | (n = 4) |
|---|---|---|---|---|
| Baseline | 5.08 ± 0.34 | 3.61 ± 0.23 | 4.44 ± 0.70 | 3.62 ± 0.56 |
| Captopril | 4.92 ± 0.33 |  | 4.39 ± 0.81 | 3.94 ± 0.53 |
| SQ 28,603 |  |  |  |  |
| 30' | 5.03 ± 0.35 | 3.36 ± 0.28* | 4.44 ± 0.70 | 5.28 ± .62* |
| 60' | 5.52 ± 0.57 | 3.50 ± 0.34 | 4.08 ± 0.63 | 5.48 ± 0.68 |
| 90' | 5.19 ± 0.48 | 3.58 ± 0.37 | 4.05 ± 0.61 | 4.34 ± 0.40 |
| 120' | 5.35 ± 0.45 | 3.60 ± 0.34 | 4.25 ± 0.65 | 4.13 ± 0.46 |
| 150' | 5.26 ± 0.43 | 3.53 ± 0.30 | 4.26 ± 0.65 | 3.63 ± 0.37 |
| 180' | 5.32 ± 0.44 | 3.70 ± 0.31 | 4.07 ± 0.65 | 3.59 ± 0.32 |
| 210' | 5.77 ± 0.45 | 3.96 ± 0.41 | 4.16 ± 0.65 | 3.74 ± 0.52 |

Change from Baseline (ml/beat)

| Vehicle | SQ 28,603 | Captopril | Captopril + SQ 28,603 |
|---|---|---|---|
| −0.05 ± 0.08 | −0.25 ± 0.13 | 0.01 ± 0.13 | 1.66 ± .20* |
| 0.45 ± 0.47 | −0.11 ± 0.17 | −0.35 ± 0.32 | 1.86 ± .41* |
| 0.11 ± 0.30 | −0.04 ± 0.20 | −0.39 ± 0.26 | 0.72 ± 0.39 |
| 0.27 ± 0.31 | −0.01 ± 0.17 | −0.19 ± 0.26 | 0.51 ± 0.43 |
| 0.18 ± 0.32 | −0.08 ± 0.15 | −0.18 ± 0.35 | 0.01 ± 0.32 |
| 0.24 ± 0.33 | 0.09 ± 0.21 | −0.36 ± 0.32 | −0.03 ± 0.25 |
| 0.69 ± 0.51 | 0.35 ± 0.34 | −0.27 ± 0.29 | 0.12 ± 0.27 |

Systemic Vascular Resistance (mm Hg/l/min)

| Time (min) | Vehicle | SQ 28,603 | Captopril | Captopril + SQ 28,603 |
|---|---|---|---|---|
|  | (n = 6) | (n = 8) | (n = 5) | (n = 4) |
| Baseline | 66 ± 4 | 96 ± 12 | 80 ± 18 | 98 ± 27 |
| Captopril | 72 ± 5 |  | 83 ± 26 | 79 ± 22 |
| SQ 28,603 |  |  |  |  |
| 30' | 69 ± 6 | 107 ± 14* | 77 ± 19 | 57 ± 15* |
| 60' | 63 ± 9 | 108 ± 14* | 82 ± 21 | 49 ± 13* |
| 90' | 66 ± 7 | 105 ± 14* | 85 ± 21 | 66 ± 18 |
| 120' | 62 ± 7 | 105 ± 13* | 84 ± 21 | 75 ± 20 |
| 150' | 65 ± 6 | 106 ± 13* | 82 ± 19 | 87 ± 22* |
| 180' | 65 ± 6 | 101 ± 12 | 87 ± 22 | 88 ± 22 |
| 210' | 66 ± 6 | 97 ± 13 | 86 ± 21 | 84 ± 22 |

Change from Baseline (mm Hg/l/min)

| Vehicle | SQ 28,603 | Captopril | Captropril + SQ 28,603 |
|---|---|---|---|
| 4 ± 3 | 12 ± 3 | −4 ± 4 | −42 ± 8* |
| 4 ± 4 | 12 ± 3 | 1 ± 7 | −49 ± 8* |
| 4 ± 3 | 9 ± 4 | 4 ± 5 | −32 ± 8* |
| 2 ± 3 | 9 ± 3 | 4 ± 6 | −23 ± 7* |
| 2 ± 3 | 10 ± 4 | 2 ± 6 | −11 ± 6 |
| 2 ± 3 | 5 ± 5 | 7 ± 7 | −10 ± 7 |
| 1 ± 3 | 2 ± 7 | 6 ± 6 | −14 ± 9 |

Renal Vascular Resistance (mm Hg/ml/min)

| Time (min) | Vehicle | SQ 28,603 | Captopril | Captopril + SQ 28,603 |
|---|---|---|---|---|
|  | (n = 4) | (n = 6) | (n = 4) | (n = 3) |
| Baseline | 1.05 ± 0.12 | 1.22 ± 0.10 | 0.91 ± 0.06 | 1.39 ± 0.28 |
| Captopril | 1.05 ± 0.09 |  | 0.74 ± 0.13 | 1.07 ± 0.29 |
| SQ 28,603 |  |  |  |  |
| 30' | 1.02 ± 0.12 | 1.28 ± 0.11 | 0.70 ± 0.07 | 0.71 ± 0.14 |
| 60' | 0.93 ± 0.11 | 1.24 ± 0.10* | 0.69 ± 0.08 | 0.58 ± 0.08* |
| 90' | 0.91 ± 0.13 | 1.18 ± 0.08* | 0.74 ± 0.05 | 0.69 ± 0.11 |
| 120' | 0.89 ± 0.13 | 1.16 ± 0.09 | 0.73 ± 0.09 | 0.81 ± 0.11 |
| 150' | 0.90 ± 0.12 | 1.12 ± 0.09 | 0.75 ± 0.12 | 0.90 ± 0.15 |
| 180' | 0.89 ± 0.10 | 1.08 ± 0.09 | 0.75 ± 0.08 | 0.99 ± 0.18 |
| 210' | 0.86 ± 0.09 | 1.07 ± 0.10 | 0.75 ± 0.09 | 0.98 ± 0.22 |

Change from Baseline (mm Hgml/min)

| Vehicle | SQ 28,603 | Captopril | Captopril + SQ 28,603 |
|---|---|---|---|
| −0.02 ± 0.05 | 0.06 ± 0.04 | −0.20 ± 0.06 | −0.68 ± .14* |
| −0.12 ± 0.07 | 0.02 ± 0.05 | −0.22 ± 0.07 | −0.81 ± .23* |
| −0.14 ± 0.10 | −0.04 ± 0.06 | −0.17 ± 0.04 | −0.70 ± .18* |
| −0.16 ± 0.11 | −0.06 ± 0.06 | −0.18 ± 0.08 | −0.58 ± .18* |
| −0.15 ± 0.10 | −0.10 ± 0.07 | −0.15 ± 0.10 | −0.49 ± 0.14 |
| −0.16 ± 0.09 | −0.14 ± 0.04 | −0.16 ± 0.08 | −0.40 ± 0.11 |
| −0.19 ± 0.10 | −0.16 ± 0.02 | −0.16 ± 0.08 | −0.41 ± 0.11 |

Renal Blood Flowml/min)

Captopril +

TABLE 1-continued

Hemodynamic, renal and hormonal responses to SQ28,603
in dogs treated with captopril during thre first week
of rapid ventricular pacing

| Time (min) | Vehicle | SQ 28,603 | Captopril | SQ 28,603 |
|---|---|---|---|---|
| | (n = 4) | (n = 6) | (n = 4) | (n = 3) |
| Baseline | 89 ± 11 | 72 ± 7 | 93 ± 7 | 62 ± 12 |
| Captopril | 89 ± 8 | | 113 ± 22 | 75 ± 16 |
| SQ 28,603 | | | | |
| 30' | 93 ± 11 | 70 ± 6 | 114 ± 7 | 102 ± 16 |
| 60' | 99 ± 10 | 73 ± 7 | 115 ± 8 | 113 ± 15 |
| 90' | 101 ± 11 | 76 ± 7 | 111 ± 6 | 102 ± 15 |
| 120' | 102 ± 10 | 79 ± 8 | 116 ± 9 | 94 ± 14 |
| 150' | 100 ± 10 | 82 ± 8 | 115 ± 11 | 88 ± 15 |
| 180' | 100 ± 8 | 85 ± 9 | 112 ± 6 | 82 ± 15 |
| 210' | 103 ± 8 | 87 ± 9 | 114 ± 7 | 83 ± 18 |

Change from Baseline (ml/min)

| Vehicle | SQ 28,603 | Captopril | Captopril + SQ 28,603 |
|---|---|---|---|
| 4 ± 2 | −2 ± 2 | 21 ± 4* | 40 ± 5* |
| 10 ± 5 | 1 ± 2 | 22 ± 5* | 51 ± 4* |
| 12 ± 9 | 5 ± 2 | 18 ± 2 | 41 ± 5* |
| 13 ± 9 | 7 ± 2 | 23 ± 7 | 32 ± 5* |
| 11 ± 7 | 10 ± 1 | 22 ± 9 | 26 ± 6 |
| 11 ± 7 | 14 ± 2 | 19 ± 7 | 21 ± 6 |
| 14 ± 8 | 16 ± 2 | 21 ± 5 | 21 ± 10 |

Glomerular Filtration Rate (ml/min)

| Time (min) | Vehicle | SQ 28,603 | Captopril | Captopril + SQ 28,603 |
|---|---|---|---|---|
| | (n = 5) | (n = 8) | (n = 5) | (n = 4) |
| Baseline | 65 ± 6 | 44 ± 4 | 58 ± 6 | 39 ± 4 |
| Captopril | 62 ± 6 | | 60 ± 13 | 50 ± 5 |
| SQ 28,603 | | | | |
| 30' | 55 ± 6 | 48 ± 4 | 73 ± 10 | 48 ± 11 |
| 60' | 76 ± 7 | 38 ± 2 | 71 ± 11 | 56 ± 9 |
| 90' | 75 ± 5 | 43 ± 4 | 66 ± 8 | 50 ± 11 |
| 120' | 79 ± 3 | 53 ± 9 | 77 ± 10 | 42 ± 13 |
| 150' | 75 ± 6 | 47 ± 5 | 79 ± 7 | 59 ± 9 |
| 180' | 81 ± 7 | 48 ± 6 | 70 ± 4 | 53 ± 4 |
| 210' | 73 ± 7 | 51 ± 4 | 88 ± 7 | 49 ± 10 |

Change from Baseline (ml/min)

| Vehicle | SQ 28,603 | Captopril | Captopril + SQ 28,603 |
|---|---|---|---|
| −10 ± 3 | 3 ± 4 | 15 ± 10 | 9 ± 8 |
| 11 ± 6 | −6 ± 3* | 12 ± 8 | 18 ± 6 |
| 10 ± 4 | −1 ± 4 | 8 ± 4 | 11 ± 7 |
| 13 ± 7 | 8 ± 6 | 18 ± 11 | 3 ± 13 |
| 9 ± 4 | 3 ± 4 | 20 ± 3 | 20 ± 6 |
| 15 ± 6 | 4 ± 5 | 12 ± 6 | 14 ± 3 |
| 8 ± 8 | 7 ± 4 | 30 ± 4* | 10 ± 8 |

Sodium Excretion (µEq/min)

| Time (min) | Vehicle | SQ 28,603 | Captopril | Captopril + SQ 28,603 |
|---|---|---|---|---|
| | (n = 6) | (n = 8) | (n = 5) | (n = 4) |
| Baseline | 7 ± 1 | 15 ± 4 | 7 ± 3 | 19 ± 8 |
| Captopril | 13 ± 4 | | 26 ± 12 | 92 ± 39 |
| SQ 28,603 | | | | |
| 30' | 16 ± 5 | 75 ± 26* | 62 ± 24 | 151 ± 89 |
| 60' | 23 ± 7 | 96 ± 24* | 86 ± 43 | 159 ± 110* |
| 90' | 40 ± 12 | 120 ± 30* | 98 ± 42 | 233 ± 111 |
| 120' | 48 ± 13 | 144 ± 36* | 132 ± 62 | 200 ± 86 |
| 150' | 56 ± 13 | 160 ± 38 | 140 ± 61 | 259 ± 46 |
| 180' | 72 ± 18 | 173 ± 51 | 139 ± 55 | 225 ± 39 |
| 210' | 81 ± 25 | 154 ± 35 | 168 ± 46 | 151 ± 48 |

Fractional Sodium Excretion (%)

| Vehicle | SQ 28,603 | Captopril | Captopril + SQ 28,603 |
|---|---|---|---|
| (n = 5) | (n = 8) | (n = 5) | (n = 4) |
| 0.07 ± 0.02 | 0.35 ± 0.06 | 0.10 ± 0.04 | 0.32 ± 0.12 |
| 0.14 ± 0.05 | | 0.37 ± 0.18 | 1.19 ± 0.42 |
| 0.22 ± 0.08 | 1.26 ± 0.36 | 0.74 ± 0.37 | 1.70 ± 0.66 |
| 0.22 ± 0.07 | 2.07 ± 0.44* | 1.03 ± 0.58 | 1.53 ± 0.91 |
| 0.36 ± 0.09 | 2.30 ± 0.35* | 1.25 ± 0.65 | 2.63 ± 0.84 |
| 0.42 ± 0.12 | 2.61 ± 0.41* | 1.57 ± 1.01 | 3.08 ± 0.49 |
| 0.50 ± 0.12 | 3.18 ± 0.55* | 1.31 ± 0.63 | 2.87 ± 0.25* |

TABLE 1-continued

Hemodynamic, renal and hormonal responses to SQ28,603
in dogs treated with captopril during thre first week
of rapid ventricular pacing

| | | | |
|---|---|---|---|
| 0.61 ± 0.16 | 3.13 ± 0.48* | 1.38 ± 0.60 | 2.75 ± 0.28 |
| 0.74 ± 0.23 | 2.64 ± 0.30* | 1.31 ± 0.38 | 1.90 ± 0.53 |

Urine Volume (ml/min)

| Time (min) | Vehicle | SQ 28,603 | Captopril | Captopril + SQ 28,603 |
|---|---|---|---|---|
| | (n = 6) | (n = 8) | (n = 5) | (n = 4) |
| Baseline | 0.5 ± 0.1 | 0.3 ± 0.1 | 0.2 ± 0.0 | 0.2 ± 0.0 |
| Captopril | 0.6 ± 0.2 | | 0.4 ± 0.1 | 0.5 ± 0.2 |
| SQ 28,603 | | | | |
| 30' | 0.3 ± 0.0 | 0.7 ± 0.1 | 0.5 ± 0.1 | 0.7 ± 0.3 |
| 60' | 0.3 ± 0.1 | 0.7 ± 0.1 | 0.6 ± 0.1 | 0.9 ± 0.4 |
| 90' | 0.4 ± 0.1 | 0.8 ± 0.1 | 0.7 ± 0.2 | 1.0 ± 0.4 |
| 120' | 0.4 ± 0.1 | 1.0 ± 0.1 | 1.0 ± 0.3 | 0.9 ± 0.3 |
| 150' | 0.4 ± 0.1 | 1.1 ± 0.1* | 0.9 ± 0.4 | 1.3 ± 0.3* |
| 180' | 0.5 ± 0.0 | 1.0 ± 0.1 | 0.9 ± 0.4 | 1.0 ± 0.1 |
| 210' | 0.5 ± 0.1 | 1.2 ± 0.1 | 1.0 ± 0.3 | 0.7 ± 0.2 |

Urinary ANP Excretion (fmole/min)

| Vehicle | SQ 28,603 | Captopril | Captopril + SQ 28,603 |
|---|---|---|---|
| | (n = 4) | | |
| | 3 ± 1 | | 4 ± 1 |
| | | | 5 ± 1 |
| | 590 ± 371** | | 602 ± 312** |
| | 1120 ± 764** | | 723 ± 261** |
| | 640 ± 458** | | 478 ± 347** |
| | 191 ± 43** | | 137 ± 44** |
| | 128 ± 47** | | 64 ± 2** |
| | 54 ± 11** | | 42 ± 10** |
| | 21 ± 5** | | 23 ± 11** |

Cyclic GMP Excretion (pmole/min)

| Time (min) | Vehicle | SQ 28,603 | Captopril | Captopril + SQ 28,603 |
|---|---|---|---|---|
| | (n = 6) | (n = 8) | (n = 5) | (n = 4) |
| Baseline | 3278 ± 509 | 2110 ± 253 | 2528 ± 266 | 746 ± 58 |
| Captopril | 3116 ± 491 | | 2356 ± 580 | 1665 ± 402 |
| SQ 28,603 | | | | |
| 30' | 2085 ± 164 | 3103 ± 531 | 2685 ± 406 | 2343 ± 309 |
| 60' | 2665 ± 299 | 3626 ± 277 | 2988 ± 775 | 3120 ± 462 |
| 90' | 2190 ± 304 | 3721 ± 372 | 3225 ± 1118 | 2772 ± 872 |
| 120' | 2590 ± 264 | 5064 ± 1165 | 2706 ± 345 | 3548 ± 979 |
| 150' | 3047 ± 542 | 4126 ± 390 | 2594 ± 459 | 3182 ± 941 |
| 180' | 3154 ± 420 | 4298 ± 504 | 2312 ± 464 | 4348 ± 902 |
| 210' | 3064 ± 347 | 4361 ± 626 | 2798 ± 436 | 2919 ± 806 |

Change from Baseline (pmole/min)

| Vehicle | SQ 28,603 | Captopril | Captopril + SQ 28,603 |
|---|---|---|---|
| (n = 6) | (n = 8) | (n = 5) | (n = 4) |
| −162 ± 470 | | −170 ± 363 | 919 ± 413 |
| −1193 ± 661 | 987 ± 596 | 158 ± 394 | 1598 ± 334* |
| −613 ± 345 | 1510 ± 300* | 460 ± 542 | 2374 ± 513* |
| −1088 ± 572 | 1605 ± 555* | 697 ± 896 | 2025 ± 920 |
| −688 ± 316 | 2948 ± 1022* | 178 ± 356 | 2802 ± 978* |
| −231 ± 362 | 2010 ± 527* | 66 ± 689 | 2436 ± 941* |
| 164 ± 164 | 2182 ± 441* | −215 ± 496 | 3602 ± 944* |
| −214 ± 461 | 2244 ± 508* | 270 ± 528 | 2173 ± 792* |

Plasma Cyclic GMP (pmole/min)

| Time (min) | Vehicle | SQ 28,603 | Captopril | Captopril + SQ 28,603 |
|---|---|---|---|---|
| | (n = 5) | (n = 8) | (n = 4) | (n = 4) |
| Baseline | 10 ± 2 | 21 ± 4 | 10 ± 2 | 32 ± 2 |
| SQ 28,603 | | | | |
| 120' | 21 ± 6 | 40 ± 6 | 20 ± 1 | 41 ± 3 |
| 240' | 35 ± 6 | 39 ± 3 | 30 ± 3 | 47 ± 4 |

Plasma Renin Activity (pmol AI/ml/hr)

| | Time (min) | Vehicle | SQ 28,603 |
|---|---|---|---|
| | | (n = 6) | (n = 8) |
| Baseline | 3.5 ± 1.1 | 2.7 ± 0.2 | 1.6 ± 0.3 | 2.0 ± 0.3 |
| SQ 28,603 | | | |
| 120' | 3.1 ± 1.9 | 1.4 ± 0.2 | 3.4 ± 1.3 | 9.8 ± 2.0* |
| 240' | 3.6 ± 2.1 | 2.2 ± 0.3 | 4.2 ± 2.2 | 11.1 ± 3.6* |

TABLE 1-continued

Hemodynamic, renal and hormonal responses to SQ28,603
in dogs treated with captopril during thre first week
of rapid ventricular pacing

Plasma ANP (fmole/ml)

| Vehicle | SQ 28,603 | Captopril | Captopril + SQ 28,603 |
|---|---|---|---|
| (n = 5) | (n = 8) | (n = 4) | (n = 4) |
| 99 ± 19 | 75 ± 10 | 87 ± 10 | 54 ± 10 |
|  | 178 ± 47 | 98 ± 11 | 120 ± 30 |
| 92 ± 15 |  |  |  |
| 96 ± 18 | 124 ± 22 | 85 ± 13 | 124 ± 24 |

|  |  | Captopril | Captopril + SQ 28,603 |
|---|---|---|---|
|  |  | (n = 4) | (n = 4) |

*$p < 0.05$ vs Vehicle;
$p < 0.05$ vs Captopril;
$p < 0.05$ vs SQ 28,603;
**$p < 0.05$ vs Baseline

TABLE 2

Hemodynamic, renal and hormonal responses to
SQ28,603 (10 μmol/kg, iv) in dogs treated with
captopril (10 μmol/kg, iv) during the third week of rapid ventricular pacing.

Left Atrial Pressure (mm Hg)

| Time (min) | Vehicle | SQ 28,603 | Captopril | Captopril + SQ 28,603 |
|---|---|---|---|---|
|  | (n = 3) | (n = 4) | (n = 4) | (n = 8) |
| Baseline | 26.8 ± 5.6 | 28.6 ± 2.2 | 27.5 ± 1.3 | 29.9 ± 2.5 |
| Captopril | 28.0 ± 5.5 |  | 25.9 ± 2.1 | 28.4 ± 1.4 |
| SQ 28,603 |  |  |  |  |
| 30' | 27.4 ± 5.1 | 29.7 ± 2.1 | 25.2 ± 2.2 | 26.3 ± 1.4 |
| 60' | 26.9 ± 5.4 | 29.1 ± 1.9 | 24.7 ± 2.2 | 25.3 ± 2.0 |
| 90' | 26.7 ± 5.4 | 27.9 ± 2.1 | 26.0 ± 1.5 | 26.6 ± 1.6 |
| 120' | 25.8 ± 5.2 | 27.6 ± 2.0 | 25.3 ± 1.5 | 27.1 ± 1.4 |
| 150' | 26.2 ± 5.2 | 27.4 ± 1.7 | 24.8 ± 1.8 | 26.8 ± 1.9 |
| 180' | 26.1 ± 5.0 | 26.9 ± 1.9 | 26.0 ± 1.3 | 27.6 ± 1.9 |
| 210' | 26.9 ± 4.9 | 26.4 ± 1.8 | 26.6 ± 1.6 | 27.8 ± 1.9 |

Change from Baseline (mm Hg)

| Vehicle | SQ 28,603 | Captopril | Captopril + SQ 28,603 |
|---|---|---|---|
| 0.65 ± 0.80 | 1.10 ± 0.88 | −2.48 ± 1.01 | −3.59 ± 1.08* |
| 0.10 ± 1.21 | 0.50 ± 1.02 | −1.90 ± 1.10 | −4.57 ± 0.86* |
| −0.07 ± 1.05 | −0.70 ± 0.79 | −0.93 ± 0.77 | −3.35 ± 0.96 |
| −1.03 ± 1.24 | −1.09 ± 0.84 | −2.25 ± 0.32 | −2.81 ± 1.14 |
| −0.56 ± 0.82 | −1.22 ± 1.08 | −2.76 ± 0.81 | −3.12 ± 1.31 |
| −0.61 ± 1.28 | −1.72 ± 1.40 | −1.49 ± 0.44 | −2.30 ± 1.24 |
| 0.05 ± 0.86 | −2.24 ± 2.28 | −0.94 ± 0.92 | −2.16 ± 1.67 |

Mean Arterial Pressure (mm Hg)

| Time (min) | Vehicle | SQ 28,603 | Captopril | Captopril + SQ 28,603 |
|---|---|---|---|---|
|  | (n = 5) | (n = 5) | (n = 4) | (n = 8) |
| Baseline | 95 ± 3 | 84 ± 2 | 104 ± 4 | 88 ± 5 |
| Captopril | 99 ± 5 |  | 101 ± 5 | 82 ± 7 |
| SQ 28,603 |  |  |  |  |
| 30' | 98 ± 5 | 85 ± 3 | 102 ± 5* | 78 ± 6* |
| 60' | 96 ± 5 | 87 ± 4 | 102 ± 5* | 79 ± 5 |
| 90' | 96 ± 5 | 84 ± 2 | 104 ± 3* | 82 ± 6 |
| 120' | 94 ± 6 | 85 ± 2 | 103 ± 5 | 83 ± 6 |
| 150' | 97 ± 7 | 84 ± 2 | 103 ± 5 | 83 ± 5 |
| 180' | 98 ± 6 | 85 ± 2 | 103 ± 4 | 85 ± 5 |
| 210' | 98 ± 6 | 85 ± 2 | 106 ± 6* | 86 ± 6 |

Change from Baseline (mm Hg)

| Vehicle | SQ 28,603 | Captopril | Captopril + SQ 28,603 |
|---|---|---|---|
| 3 ± 2 | 1 ± 1 | −2 ± 2 | −10 ± 2* |
| 1 ± 2 | 2 ± 2 | −2 ± 2 | −9 ± 1* |
| 1 ± 2 | 0 ± 1 | 1 ± 1 | −5 ± 1* |
| −1 ± 2 | 1 ± 1 | −2 ± 1 | −4 ± 2 |
| 2 ± 4 | 0 ± 1 | 1 ± 2 | −5 ± 1 |
| 3 ± 3 | 1 ± 2 | −1 ± 1 | −3 ± 1 |
| 3 ± 2 | 1 ± 1 | 2 ± 3 | −2 ± 1 |

Cardiac Output (l/min)

TABLE 2-continued

Hemodynamic, renal and hormonal responses to
SQ28,603 (10 μmol/kg, iv) in dogs treated with
captopril (10 μmol/kg, iv) during the third week of rapid ventricular pacing.

| Time (min) | Vehicle | SQ 28,603 | Captopril | Captopril + SQ 28,603 |
|---|---|---|---|---|
|  | (n = 5) | (n = 5) | (n = 4) | (n = 8) |
| Baseline | 0.09 ± 0.23 | 0.63 ± 0.05 | 0.90 ± 0.22 | 0.74 ± 0.11 |
| Captopril | 0.88 ± 0.23 |  | 0.94 ± 0.25 | 0.97 ± 0.13 |
| SQ 28,603 |  |  |  |  |
| 30' | 0.86 ± 0.22 | 0.65 ± 0.08 | 0.73 ± 0.14* | 1.09 ± 0.13 |
| 60' | 0.88 ± 0.21 | 0.68 ± 0.09 | 0.81 ± 0.18 | 1.01 ± 0.18 |
| 90' | 0.90 ± 0.22 | 0.66 ± −.09 | 0.88 ± 0.2−0 | 0.93 ± 0.15 |
| 120' | 0.90 ± 0.20 | 0.69 ± 0.09 | 1.03 ± 0.23 | 0.92 ± 0.15 |
| 150' | 0.96 ± 0.22 | 0.66 ± 0.11 | 0.92 ± 0.17 | 0.86 ± 0.15 |
| 180' | 1.01 ± 0.21 | 0.66 ± 0.10 | 0.93 ± 0.20 | 0.91 ± 0.16 |
| 210' | 1.02 ± 0.23 | 0.70 ± 0.10 | 1.04 ± 0.16 | 0.89 ± 0.16 |

Change from Baseline (l/min)

| Vehicle | SQ 28,603 | Captopril | Captopril + SQ 28,603 |
|---|---|---|---|
| −0.05 ± 0.03 | 0.02 ± 0.04 | 0.05 ± 0.08 | 0.34 ± .04* |
| −0.02 ± 0.05 | 0.06 ± 0.05 | −0.02 ± 0.06 | 0.28 ± .08* |
| 0.00 ± 0.06 | 0.03 ± 0.06 | 0.07 ± 0.04 | 0.03 ± 0.06 |
| −0.01 ± 0.05 | 0.06 ± 0.05 | 0.18 ± 0.05 | 0.18 ± 0.05 |
| 0.06 ± 0.06 | 0.03 ± 0.09 | 0.22 ± 0.04 | 0.12 ± 0.05 |
| 0.10 ± 0.06 | 0.03 ± 0.07 | 0.14 ± 0.10 | 0.17 ± 0.06 |
| 0.12 ± 0.08 | 0.07 ± 0.07 | 0.26 ± 0.15 | 0.16 ± 0.06 |

Stroke Volume (ml/beat)

| Time (min) | Vehicle | SQ 28,603 | Captopril | Captopril + SQ 28,603 |
|---|---|---|---|---|
|  | (n = 5) | (n = 8) | (n = 4) | (n = 8) |
| Baseline | 3.54 ± 0.85 | 2.48 ± 0.20 | 3.21 ± 0.75 | 2.83 ± 0.42 |
| Captopril | 3.44 ± 0.88 |  | 3.83 ± 1.00 | 3.72 ± 0.48 |
| SQ 28,603 | 3.37 ± 0.82 | 2.56 ± 0.34 | 2.98 ± 0.59* | 4.15 ± 0.50* |
| 30' |  |  |  |  |
| 60' | 3.48 ± 0.78 | 2.72 ± 0.38 | 3.31 ± 0.69 | 3.90 ± 0.67 |
| 90' | 3.54 ± 0.81 | 2.61 ± 0.39 | 3.57 ± 0.82 | 3.57 ± 0.58 |
| 120' | 3.43 ± 0.76 | 2.72 ± 0.36 | 4.20 ± 0.92 | 3.42 ± 0.56 |
| 150' | 3.78 ± 0.82 | 2.64 ± 0.48 | 3.78 ± 0.73 | 3.31 ± 0.58 |
| 180' | 3.95 ± 0.78 | 2.61 ± 0.43 | 3.82 ± 0.88 | 3.49 ± 0.63 |
| 210' | 4.02 ± 0.87 | 2.78 ± 0.43 | 4.32 ± 0.79 | 3.43 ± 0.63 |

Change from Baseline (ml/beat)

| Vehicle | SQ 28,603 | Captopril | Captopril + SQ 28,603 |
|---|---|---|---|
| −0.18 ± 0.13 | 0.09 ± 0.17 | 0.16 ± 0.31 | 1.32 ± .16* |
| −0.07 ± 0.19 | 0.24 ± 0.23 | −0.08 ± 0.23 | 1.06 ± .29* |
| 0.00 ± 0.24 | 0.13 ± 0.24 | 0.27 ± 0.24 | 0.74 ± 0.21 |
| −0.02 ± 0.20 | 0.24 ± 0.22 | 0.77 ± 0.24 | 0.69 ± 0.19 |
| 0.23 ± 0.22 | 0.16 ± 0.35 | 0.90 ± 0.17 | 0.47 ± 0.20 |
| 0.40 ± 0.22 | 0.13 ± 0.30 | 0.61 ± 0.43 | 0.66 ± 0.23 |
| 0.47 ± 0.29 | 0.30 ± 0.31 | 1.103 ± 0.64 | 0.59 ± 0.22 |

Systemic Vascular Resistance (mm Hg/l/min)

| Time (min) | Vehicle | SQ 28,603 | Captopril | Captopril + SQ 28,603 |
|---|---|---|---|---|
|  | (n = 6) | (n = 8) | (n = 4) | (n = 8) |
| Baseline | 118 ± 28 | 127 ± 10 | 149 ± 52 | 121 ± 14 |
| Captopril | 132 ± 31 |  | 132 ± 51 | 84 ± 9 |
| SQ 28,603 |  |  |  |  |
| 30' | 128 ± 27 | 125 ± 11 | 146 ± 46 | 72 ± 9 |
| 60' | 113 ± 20 | 120 ± 12 | 133 ± 43 | 82 ± 11 |
| 90' | 112 ± 19 | 122 ± 13 | 131 ± 45 | 89 ± 12 |
| 120' | 110 ± 18 | 117 ± 12 | 110 ± 38 | 90 ± 10 |
| 150' | 106 ± 21 | 123 ± 15 | 116 ± 37 | 98 ± 12 |
| 180' | 98 ± 19 | 124 ± 13 | 133 ± 56 | 94 ± 11* |
| 210' | 104 ± 24 | 114 ± 11 | 101 ± 31 | 96 ± 12 |

Change from Baseline (mm Hg/l/min)

| Vehicle | SQ 28,603 | Captopril | Captopril + SQ 28,603 |
|---|---|---|---|
| 10 ± 6 | −1 ± 9 | −10 ± 14 | −54 ± 9* |
| −5 ± 13 | −6 ± 10 | −13 ± 17 | −43 ± 6* |
| −5 ± 14 | −4 ± 12 | −15 ± 14 | −33 ± 5 |
| −7 ± 16 | −10 ± 12 | −38 ± 15 | −32 ± 5 |
| −11 ± 10 | −4 ± 16 | −24 ± 4 | −36 ± 14 |
| −19 ± 10 | −3 ± 12 | −15 ± 24 | −25 ± 4 |
| −14 ± 5 | −13 ± 12 | −48 ± 27 | −23 ± 5 |

TABLE 2-continued

Hemodynamic, renal and hormonal responses to
SQ28,603 (10 μmol/kg, iv) in dogs treated with
captopril (10 μmol/kg, iv) during the third week of rapid ventricular pacing.

Renal Vascular Resistance (mm Hg/ml/min)

| Time (min) | Vehicle | SQ 28,603 | Captopril | Captopril + SQ 28,603 |
|---|---|---|---|---|
| | (n = 2) | (n = 5) | (n = 3) | (n = 7) |
| Baseline | 1.23 ± 0.03 | 1.36 ± 0.24 | 1.72 ± 0.17 | 2.44 ± 0.18 |
| Captopril | 1.30 ± 0.05 | | 1.40 ± 0.10 | 1.12 ± 0.14 |
| SQ 28,603 | | | | |
| 30' | 1.22 ± 0.02 | 1.38 ± 0.28 | 1.38 ± 0.20 | 0.85 ± 0.10 |
| 60' | 1.18 ± 0.04 | 1.30 ± 0.27 | 1.38 ± 0.14 | 0.87 ± 0.09 |
| 90' | 1.21 ± 0.03 | 1.18 ± 0.20 | 1.40 ± 0.16 | 0.97 ± 0.13 |
| 120' | 1.17 ± 0.03 | 1.15 ± 0.20 | 1.32 ± 0.16 | 0.98 ± 0.14 |
| 150' | 1.16 ± 0.00 | 1.10 ± 0.19 | 1.32 ± 0.20 | 0.97 ± 0.11 |
| 180' | 1.21 ± 0.06 | 1.07 ± 0.19 | 1.28 ± 0.11 | 1.03 ± 0.12 |
| 210' | 1.21 ± 0.06 | 1.07 ± 0.19 | 1.28 ± 0.11 | 1.03 ± 0.12 |

Change from Baseline (mm Hgml/min)

| Vehicle | SQ 28,603 | Captopril | Captopril + SQ 28,603 |
|---|---|---|---|
| −0.01 ± 0.01 | 0.02 ± 0.04 | −0.33 ± 0.03 | −0.60 ± 0.14* |
| −0.05 ± 0.01 | −0.06 ± 0.05 | −0.34 ± 0.04 | −0.58 ± 0.11* |
| −0.02 ± 0.00 | −0.18 ± 0.05 | −0.32 ± 0.02 | −0.48 ± 0.09* |
| −0.06 ± 0.00 | −0.21 ± 0.06 | −0.39 ± 0.03 | −0.46 ± 0.09* |
| −0.07 ± 0.03 | −0.26 ± 0.09 | −0.40 ± 0.04 | −0.47 ± 0.08 |
| −0.02 ± 0.09 | −0.29 ± 0.08 | −0.43 ± 0.08 | −0.42 ± 0.07 |
| 0.23 ± 0.14 | −0.30 ± 0.07* | −0.43 ± 0.10* | −0.40 ± 0.07* |

Renal Blood Flowml/min)

| Time (min) | Vehicle | SQ 28,603 | Captopril | Captopril + SQ 28,603 |
|---|---|---|---|---|
| | (n = 2) | (n = 5) | (n = 3) | (n = 7) |
| Baseline | 63 ± 2 | 62 ± 10 | 55 ± 3 | 55 ± 7 |
| Captopril | 65 ± 2 | | 64 ± 1 | 62 ± 6 |
| SQ 28,603 | | | | |
| 30' | 66 ± 1 | 63 ± 11 | 66 ± 6 | 78 ± 7 |
| 60' | 67 ± 1 | 67 ± 12 | 67 ± 4 | 78 ± 7 |
| 90' | 66 ± 0 | 69 ± 11 | 68 ± 4 | 76 ± 9 |
| 120' | 66 ± 0 | 72 ± 11 | 70 ± 4 | 77 ± 9 |
| 150' | 67 ± 1 | 74 ± 12 | 74 ± 6 | 75 ± 8 |
| 180' | 66 ± 2 | 77 ± 13 | 72 ± 2 | 73 ± 8 |
| 210' | 65 ± 2 | 79 ± 14 | 75 ± 3 | 74 ± 8 |

Change from Baseline (ml/min)

| Vehicle | SQ 28,603 | Captopril | Captopril + SQ 28,603 |
|---|---|---|---|
| 2 ± 1 | 1 ± 1 | 12 ± 3 | 23 ± 4* |
| 3 ± 1 | 6 ± 2 | 12 ± 2 | 23 ± 2* |
| 2 ± 2 | 7 ± 2 | 14 ± 2 | 21 ± 4* |
| 3 ± 2 | 10 ± 3 | 15 ± 2 | 22 ± 4 |
| 4 ± 4 | 12 ± 4 | 19 ± 3 | 20 ± 3 |
| 3 ± 3 | 15 ± 6 | 18 ± 1 | 16 ± 6 |
| 2 ± 4 | 17 ± 7 | 20 ± 1 | 19 ± 2 |

Glomerular Filtration Rate (ml/min)

| Time (min) | Vehicle | SQ 28,603 | Captopril | Captopril + SQ 28,603 |
|---|---|---|---|---|
| | (n = 5) | (n = 5) | (n = 4) | (n = 4) |
| Baseline | 56 ± 8 | 40 ± 7 | 46 ± 6 | 32 ± 3 |
| Captopril | 49 ± 6 | | 56 ± 9 | 37 ± 7 |
| SQ 28,603 | | | | |
| 30' | 54 ± 7 | 41 ± 6 | 52 ± 6 | 43 ± 6 |
| 60' | 48 ± 4 | 40 ± 8 | 57 ± 5 | 47 ± 6 |
| 90' | 61 ± 6 | 41 ± 7 | 53 ± 5 | 47 ± 7 |
| 120' | 57 ± 6 | 51 ± 11 | 56 ± 8 | 51 ± 6 |
| 150' | 52 ± 6 | 43 ± 7 | 48 ± 8* | 46 ± 5 |
| 180' | 57 ± 7 | 40 ± 6 | 54 ± 10 | 46 ± 5 |
| 210' | 54 ± 6 | 48 ± 14 | 46 ± 7 | 44 ± 9 |

Change from Baseline (ml/min)

| Vehicle | SQ 28,603 | Captopril | Captopril + SQ 28,603 |
|---|---|---|---|
| −2 ± 5 | 1 ± 2 | 6 ± 2 | 11 ± 3* |
| −8 ± 4 | 0 ± 2 | 11 ± 3 | 21 ± 8* |
| 5 ± 4 | 1 ± 4 | 7 ± 3 | 14 ± 5 |
| 2 ± 5 | 11 ± 4 | 10 ± 3 | 18 ± 3* |
| −3 ± 5 | 2 ± 2 | 2 ± 6 | 14 ± 2* |
| 2 ± 4 | 0 ± 3 | 8 ± 5 | 14 ± 2* |

TABLE 2-continued

Hemodynamic, renal and hormonal responses to SQ28,603 (10 μmol/kg, iv) in dogs treated with captopril (10 μmol/kg, iv) during the third week of rapid ventricular pacing.

|  | $-2 \pm 6$ | $8 \pm 8$ | $1 \pm 6$ | $13 \pm 6$ |
|---|---|---|---|---|

Sodium Excretion (μEq/min)

| Time (min) | Vehicle | SQ 28,603 | Captopril | Captopril + SQ 28,603 |
|---|---|---|---|---|
|  | (n = 5) | (n = 5) | (n = 4) | (n = 7) |
| Baseline | 18 ± 13 | 26 ± 19 | 53 ± 33 | 16 ± 7 |
| Captopril | 25 ± 16 |  | 137 ± 53 | 49 ± 22 |
| SQ 28,603 |  |  |  |  |
| 30' | 44 ± 31 | 118 ± 78* | 145 ± 47 | 144 ± 57* |
| 60' | 55 ± 40 | 143 ± 90 | 178 ± 63 | 177 ± 62 |
| 90' | 63 ± 42 | 144 ± 91 | 196 ± 67 | 159 ± 57 |
| 120' | 68 ± 47 | 181 ± 88 | 215 ± 70 | 162 ± 51 |
| 150' | 49 ± 24 | 154 ± 78 | 188 ± 49 | 140 ± 37 |
| 180' | 67 ± 38 | 155 ± 79 | 195 ± 55 | 142 ± 38 |
| 210' | 76 ± 40 | 183 ± 87 | 158 ± 44 | 143 ± 43 |

Fractional Sodium Excretion (%)

|  | Vehicle | SQ 28,603 | Captopril | Captopril + SQ 28,603 |
|---|---|---|---|---|
|  | (n = 5) | (n = 5) | (n = 4) | (n = 7) |
|  | 0.24 ± 0.19 | 0.38 ± 0.23 | 0.62 ± 0.36 | 0.32 ± 0.13 |
|  | 0.33 ± 0.23 |  | 1.47 ± 0.49 | 0.70 ± 0.27 |
|  | 0.52 ± 0.34 | 1.62 ± 0.93 | 1.78 ± 0.54 | 1.90 ± 0.58 |
|  | 0.80 ± 0.59 | 1.92 ± 1.00 | 1.95 ± 0.62 | 2.33 ± 0.63 |
|  | 0.72 ± 0.48 | 2.01 ± 0.97 | 2.28 ± 0.63 | 2.20 ± 0.50 |
|  | 0.79 ± 0.54 | 1.95 ± 0.80 | 2.42 ± 0.65 | 2.10 ± 0.49 |
|  | 0.66 ± 0.34 | 2.05 ± 0.84 | 3.02 ± 1.16 | 2.07 ± 0.50 |
|  | 0.845 ± 0.45 | 2.16 ± 0.87 | 2.70 ± 1.10 | 1.94 ± 0.46 |
|  | 1.00 ± 0.42 | 2.12 ± 0.78 | 2.82 ± 1.24 | 1.98 ± 0.51 |

Urine Volume (ml/min)

| Time (min) | Vehicle | SQ 28,603 | Captopril | Captopril + SQ 28,603 |
|---|---|---|---|---|
|  | (n = 6) | (n = 8) | (n = 5) | (n = 4) |
| Baseline | 0.37 ± 0.06 | 0.31 ± 0.06 | 0.41 ± 0.22 | 0.25 ± 0.04 |
| Captopril | 0.29 ± 0.07 |  | 0.92 ± 0.37 | 0.41 ± 0.13 |
| SQ 28,603 |  |  |  |  |
| 30' | 0.40 ± 0.11 | 0.89 ± 0.36 | 0.82 ± 0.23 | 1.08 ± 0.36 |
| 60' | 0.43 ± 0.16 | 1.05 ± 0.51* | 1.06 ± 0.36 | 1.48 ± 0.28* |
| 90' | 0.44 ± 0.12 | 1.00 ± 0.56* | 1.07 ± 0.34 | 1.26 ± 0.24 |
| 120' | 0.50 ± 0.24 | 1.27 ± 0.49* | 1.20 ± 0.37 | 1.16 ± 0.15 |
| 150' | 0.34 ± 0.04 | 0.99 ± 0.40 | 1.08 ± 0.29 | 0.86 ± 0.10 |
| 180' | 0.45 ± 0.11 | 0.84 ± 0.34 | 1.01 ± 0.26 | 0.84 ± 0.11 |
| 210' | 0.54 ± 0.20 | 1.01 ± 0.40 | 0.88 ± 0.18 | 0.78 ± 0.16 |

Urinary ANP Excretion (fmole/min)

|  | Vehicle | SQ 28,603 | Captopril | Captopril + SQ 28,603 |
|---|---|---|---|---|
|  | (n = 2) | (n = 5) | (n = 4) | (n = 8) |
|  | 4 ± 1 | 4 ± 1 | 7 ± 2 | 5 ± 1 |
|  | 4 ± 1 |  | 5 ± 1 | 11 ± 6 |
|  | 4 ± 0 | 946 ± 474 | 9 ± 3 | 403 ± 99 |
|  | 8 ± 1 | 1334 ± 572* | 11 ± 2 | 671 ± 113* |
|  | 6 ± 1 | 1163 ± 380* | 13 ± 4 | 1254 ± 445* |
|  | 5 ± 1 | 1254 ± 445* | 11 ± 4 | 381 ± 86* |
|  | 4 ± 0 | 308 ± 1178* | 10 ± 3 | 195 ± 36* |
|  | 5 ± 1 | 159 ± 29* | 28 ± 14 | 78 ± 15* |
|  | 5 ± 1 | 70 ± 16* | 13 ± 3 | 46 ± 12* |

Cyclic GMP Excretion (pmole/min)

| Time (min) | Vehicle | SQ 28,603 | Captopril | Captopril + SQ 28,603 |
|---|---|---|---|---|
|  | (n = 5) | (n = 5) | (n = 4) | (n = 8) |
| Baseline | 1547 ± 339 | 1568 ± 130 | 1718 ± 516 | 2134 ± 474 |
| Captopril | 1078 ± 346 |  | 1760 ± 404 | 1965 ± 485 |
| SQ 28,603 |  |  |  |  |
| 30' | 1551 ± 357 | 3326 ± 882 | 2441 ± 675 | 3426 ± 1193 |
| 60' | 1777 ± 214 | 4070 ± 792 | 1995 ± 434 | 6179 ± 1875 |
| 90' | 2311 ± 615 | 4232 ± 966 | 2288 ± 610 | 7943 ± 3690 |
| 120' | 1566 ± 187 | 6239 ± 1722 | 2025 ± 368 | 7640 ± 2285 |
| 150' | 1566 ± 188 | 5766 ± 1018 | 2597 ± 861 | 6620 ± 1727 |
| 180' | 2173 ± 171 | 4138 ± 591 | 2580 ± 632 | 5332 ± 1071 |
| 210' | 2645 ± 683 | 2958 ± 624 | 2505 ± 548 | 5381 ± 2040 |

Change from Baseline (pmole/min)

|  |  |  |  | Captopril + |

TABLE 2-continued

Hemodynamic, renal and hormonal responses to SQ28,603 (10 μmol/kg, iv) in dogs treated with captopril (10 μmol/kg, iv) during the third week of rapid ventricular pacing.

| Vehicle | SQ 28,603 | Captopril | SQ 28,603 |
|---|---|---|---|
| (n = 5) | (n = 5) | (n = 4) | (n = 8) |
| 4 ± 198 | 4033 ± 2372 | 723 ± 205 | 1292 ± 906 |
| 230 ± 418 | 3235 ± 927 | 276 ± 285 | 4045 ± 1496 |
| 764 ± 785 | 4056 ± 1567 | 570 ± 159 | 5809 ± 3320 |
| 225 ± 345 | 5466 ± 1510 | 307 ± 450 | 5506 ± 2109 |
| 19 ± 463 | 4835 ± 1001* | 879 ± 441 | 4486 ± 1602* |
| 626 ± 435 | 3286 ± 870* | 862 ± 429 | 3199 ± 650* |
| 1098 ± 940 | 2509 ± 1243 | 786 ± 722 | 3248 ± 1592 |

Plasma Cyclic GMP (pmole/ml)

| Time (min) | Vehicle | SQ 28,603 | Captopril | Captopril + SQ 28,603 |
|---|---|---|---|---|
| | (n = 5) | (n = 5) | (n = 4) | (n = 8) |
| Baseline SQ 28,603 | 23 ± 8 | 66 ± 25 | 33 ± 6 | 31 ± 4 |
| 120' | 20 ± 2 | 83 ± 6* | 25 ± 7 | 56 ± 9* |
| 240' | 37 ± 2 | 66 ± 7* | 32 ± 5 | 52 ± 7* |

Plasma Renin Activity (pmol AI/ml/hr)

| | | Time (min) | Vehicle | SQ 28,603 |
|---|---|---|---|---|
| | | | (n = 5) | (n = 8) |
| Baseline SQ 28,603 | 5.1 ± 2.2 | 4.3 ± 2.6 | 1.6 ± 0.1 | 2.9 ± 0.9 |
| 120' | 3.6 ± 1.5 | 2.8 ± 1.9 | 3.2 ± 1.0 | 5.2 ± 2.2 |
| 240' | 4.6 ± 2.0 | 2.8 ± 1.8 | 4.4 ± 1.2 | 4.8 ± 1.6 |

Plasma ANP (fmol/ml)

| Vehicle | SQ 28,603 | Captopril | Captopril + SQ 28,603 |
|---|---|---|---|
| (n = 4) | (n = 5) | (n = 4) | (n = 8) |
| 88 ± 17 | 72 ± 7 | 94 ± 20 | 90 ± 24 |
| 86 ± 13 | 233 ± 37* | 82 ± 19 | 200 ± 41* |
| 87 ± 15 | 171 ± 15* | 86 ± 23 | 145 ± 27* |

| | | Captopril | Captopril + SQ 28,603 |
|---|---|---|---|
| | | (n = 4) | (n = 4) |

*p < 0.05 vs Vehicle;
 p < 0.05 vs Captopril;
 p < 0.05 vs SQ 28,603;
**p < 0.05 vs Baseline p 4. Discussion Of Results a) Dogs Paced For 7 to 14 Days The combination of captopril and SQ28,603 produced hemodynamic effects which were not seen with either treatment alone. Specifically, there were significant increases in cardiac output, stroke volume and renal blood flow and reductions in mean arterial pressure, right atrial pressure, systemic vascular resistance and renal vascular resistance.

In addition, the combination of 100 μmol/kg of captopril and 10 μmol/kg, iv of SQ28,603 increased excretion of sodium, cyclic GMP and ANP to the same extent as did 10 μmol/kg, iv of SQ28,603 given alone. In the dogs receiving the combination of captopril and SQ28,603, the natriuretic response was preserved despite the fact that renal perfusion pressure was reduced to approximately 80 mm Hg during the course of the study. Thus, the combination of captopril and SQ28,603 produced a unique profile of beneficial changes in peripheral hemodynamics and renal function in dogs with mild heart failure.

b) Dogs Paced For 21 to 24 Days

As found in the dogs paced for one week, the administration of 10 μmol/kg of SQ28,603 produced similar increases in excretion of sodium, cyclic GMP, ANP, and plasma ANP concentrations in the absence and presence of captopril. However, captopril alone simulated a natriuresis without the accompanying rises in urinary cyclic GMP or ANP excretion or plasma ANP concentrations.

In addition to the renal and hormonal effects, the combination of SQ28,603 and captopril (10 μmol/kg dose) increased cardiac output, stroke volume, and renal blood flow. During the third week of pacing, coadministration of SQ28,603 and captopril also significantly increased GFR, and indication that renal function was actually improved. There were also decreases in LAP, MAP, and renal and systemic vascular resistance not seen with either SQ28,603 or captopril alone.

What is claimed is:

1. A method of treating a mammalian specie suffering from congestive heart failure comprising administering an effective amount of a selective inhibitor of neutral endopeptidase of the formula

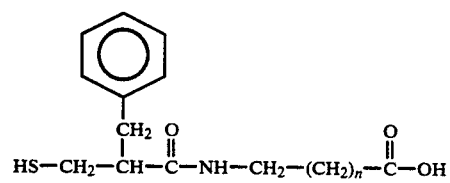

wherein n is an integer from 1 to 9 and an effective amount of an angiotensin converting enzyme inhibitor selected from the group consisting of captopril, fosinopril sodium, enalapril maleate, and lisinopril, said inhibitors being administered concurrently or at an interval of up to about 4 hours.

2. The method of claim 1 wherein the selective inhibitor of neutral endopeptidase is

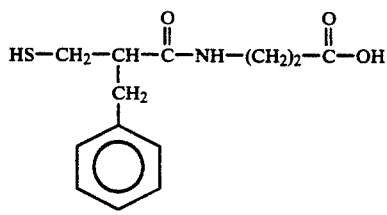

and the angiotensin converting enzyme inhibitor is captopril.

3. The method of claim 1 wherein the selective inhibitor of neutral endopeptidase and the angiotensin converting enzyme inhibitor are administered concurrently from a single dose form.

4. The method of claim 1 wherein the selective inhibitor of neutral endopeptidase and the angiotensin converting enzyme inhibitor are administered concurrently from separate dosage forms.

5. The method of claim 1 wherein the selective inhibitor of neutral endopeptidase and the angiotensin converting enzyme inhibitor are administered separately up to about 4 hours apart.

6. The method of claim 1 wherein the selective inhibitor of neutral endopeptidase is administered at a dosage range of from about 0.03 to about 1000 mg. per kg. of body weight per day and the angiotensin converting enzyme inhibitor is administered at a dosage range of from about 0.001 to about 50 mg. per kg. of body weight per day.

7. The method of claim 6 wherein the selective inhibitor of neutral endopeptidase is administered at a dosage range of from about 0.3 to about 300 mg. per kg. of body weight per day and the angiotensin converting enzyme inhibitor is administered at a dosage range of from about 0.1 to about 10 mg. per kg. of body weight per day.

* * * * *